(12) United States Patent
Gillinov et al.

(10) Patent No.: US 7,922,657 B2
(45) Date of Patent: Apr. 12, 2011

(54) SURGICAL RETRACTORS AND METHOD OF OPERATION

(76) Inventors: Alan Marc Gillinov, Orange, OH (US); Albert N. Santilli, Pepper Pike, OH (US)

( * ) Notice: Subject to any disclaimer, the term of this patent is extended or adjusted under 35 U.S.C. 154(b) by 77 days.

(21) Appl. No.: 10/513,382

(22) PCT Filed: May 5, 2003

(86) PCT No.: PCT/US03/13794
§ 371 (c)(1), (2), (4) Date: May 13, 2005

(87) PCT Pub. No.: WO2004/010859
PCT Pub. Date: Feb. 5, 2004

(65) Prior Publication Data
US 2005/0228232 A1    Oct. 13, 2005

Related U.S. Application Data

(60) Provisional application No. 60/377,929, filed on May 3, 2002.

(51) Int. Cl.
*A61B 1/32* (2006.01)
(52) U.S. Cl. ...................................................... 600/210
(58) Field of Classification Search .................. 600/184, 600/201, 206, 208, 209, 210, 213, 214, 215, 600/216, 217, 218, 219, 220, 222, 224, 225, 600/226, 227, 228, 229, 230, 232, 233, 234, 600/235
See application file for complete search history.

(56) References Cited

U.S. PATENT DOCUMENTS

| | | | | |
|---|---|---|---|---|
| 1,963,173 A | * | 6/1934 | Morin | 600/233 |
| 2,623,517 A | * | 12/1952 | Israel et. al. | 600/233 |
| 3,168,093 A | | 2/1965 | Gauthier | |
| 3,221,743 A | | 12/1965 | Thompson et al. | |
| 3,313,294 A | | 4/1967 | Uddenberg | |
| 3,467,079 A | | 9/1969 | James | |
| 4,226,228 A | | 10/1980 | Shin et al. | |
| 4,852,552 A | * | 8/1989 | Chaux | 600/232 |
| 4,865,019 A | | 9/1989 | Phillips | |
| RE34,150 E | | 12/1992 | Santilli et al. | |
| 5,167,223 A | * | 12/1992 | Koros et al. | 600/232 |
| 5,381,788 A | * | 1/1995 | Matula et al. | 600/214 |

(Continued)

OTHER PUBLICATIONS

"Seminars in Thoracic and Cardiovascular Surgery", Jan. 2000 issue; published by W.B. Saunders Publishing Company. Eleven abstracts attached.

(Continued)

*Primary Examiner* — Anu Ramana
(74) *Attorney, Agent, or Firm* — Wayne D. Porter, Jr.

(57) ABSTRACT

A first surgical retractor (302) according to the invention includes a handle (308) that defines an axis (320) and has first and second ends. A retractor blade (306) is secured to the second end of the handle. The blade is of a size and shape to engage the mitral valve of a heart so as to be able to retract the mitral valve and adjacent tissues. A second retractor (304) according to the invention has a relatively narrow, elongate blade (352) that can extend deep into the heart to engage the heart in the region of the atrial appendage so as to be able to retract the atrium and expose the pulmonary veins. The retractors are especially adapted to perform an atrial fibrillation surgical procedure.

22 Claims, 8 Drawing Sheets

U.S. PATENT DOCUMENTS

| | | | | |
|---|---|---|---|---|
| 5,456,695 A | * | 10/1995 | Dallemagne | 606/207 |
| 5,554,101 A | * | 9/1996 | Matula et al. | 600/214 |
| 5,772,583 A | | 6/1998 | Wright et al. | |
| 5,904,649 A | | 5/1999 | Andrese | |
| 5,928,139 A | | 7/1999 | Koros et al. | |
| 5,967,972 A | | 10/1999 | Santilli et al. | |
| 6,099,468 A | | 8/2000 | Santilli et al. | |
| 6,102,854 A | | 8/2000 | Cartier et al. | |
| 6,120,437 A | | 9/2000 | Yoon et al. | |
| 6,283,912 B1 | | 9/2001 | Hu et al. | |
| 6,309,349 B1 | * | 10/2001 | Bertolero et al. | 600/213 |
| 6,331,158 B1 | | 12/2001 | Hu et al. | |
| 6,464,634 B1 | * | 10/2002 | Fraser | 600/233 |

OTHER PUBLICATIONS

1.) The development of the Maze procedure for the treatment of atrial fibrillation, J.L.Cox, et al.

2.) Current status of the Maze procedure for the treatment of atrial fibrillation, J.L. Cox, et al.

3.) The importance of cryoablation of the coronary sinus during the Maze procedure, J.L.Cox,et al.

4.) The Cox-Maze procedure: The Cleveland Clinic experience, P.M. McCarthy et al.

5.) Cox-Maze procedure for atrial fibrillation: Mayo Clinic experience, H.V. Schaff, et al.

6.) The Maze procedure: the LDS Hospital experience, J.M. Arcidi, Jr., et al.

7.) Treatment of atrial fibrillation using the Maze procedure: the Japanese experience, Y. Kosakai.

8.) The Maze-III procedure combined with valve surgery, J.L. Cox, et al.

9.) Stroke Prevention as an indication for the Maze procedure in the treatment of atrial fibrillation, N. Ad, et al.

10.) Observations on the perioperative management of patients undergoing the Maze procedure, N. Ad, et al.

11.) New surgical and catheter-based modifications of the Maze procedure, J.L. Cox, et al.

* cited by examiner

SURGICAL RETRACTORS AND METHOD OF OPERATION

REFERENCE TO RELATED APPLICATION

This application claims priority to provisional Patent Application Ser. No. 60/377,929, filed May 3, 2002, by A. Marc Gillinov and Albert N. Santilli, the disclosure of which is hereby incorporated by reference in its entirety.

BACKGROUND OF THE INVENTION

1. Field of the Invention

The present invention relates generally to retractors for use in heart surgery and, more particularly, to retractors for use during open-heart surgery.

2. Description of the Prior Art

The heart is a hollow muscular pump located in the chest cavity in a loose protective sack called the pericardium. The heart is comprised of a thick muscular layer called the myocardium, which defines four chambers that include two upper chambers, the atria, and two lower chambers, the ventricles. The atrium and ventricle on the right side are separated by a tricuspid valve, while the atrium and ventricle on the left side are separated by a bicuspid (mitral) valve. The right-side atrium and ventricle are separated from the left-side atrium and ventricle by a wall known as the septum.

Normally, the heart beats in a continuous, regular rhythm. Sometimes, however, the heart beats in an irregular rhythm that frequently is caused by atrial fibrillation. Atrial fibrillation is an abnormal heart rhythm that originates in the atria. Instead of electrical impulses traveling in an orderly fashion through the heart, many impulses begin and spread through the atria, causing a rapid and disorganized heartbeat. Research has shown that the majority of undesired electrical activity (foci) come from the areas around the four pulmonary veins. Other less common areas include the superior vena cava, right and left atria, and the coronary sinus. While it once was thought that atrial fibrillation was harmless, it now is known that atrial fibrillation is associated with heart failure, blood clots, a five- to sevenfold increase in stroke, and increased mortality from heart disease.

There are a number of techniques that can be used to correct or alleviate atrial fibrillation. One popular non-surgical technique is pulmonary vein isolation ablation. In this technique, special catheters are inserted through the right atrium and the septum into the left atrium. The catheters are used for mapping locations of abnormal electrical impulses and for delivering energy to the atrium in the region of the atrium that connects to the pulmonary veins. The catheters produce circular scars that block any electrical impulses from firing within the pulmonary veins, thus preventing atrial fibrillation.

Unfortunately, non-surgical procedures such as pulmonary vein isolation ablation are not suitable to correct atrial fibrillation in all cases. Atrial fibrillation is very common, and those with atrial fibrillation often have concurrent heart disease such as coronary artery disease or valve disease that requires surgical treatment. In such cases, it is necessary to expose the heart by conducting open-heart surgery in order to have access to the interior of the heart.

During a typical open-heart surgical procedure, the chest is incised along the sternum. A thoracic retractor separates the split sternum in order to expose the heart. Specifically, the thoracic retractor includes grips that fit on either side of the incision and which can be moved apart to expose the heart. The grips maintain the incision open for the duration of the open-heart surgical procedure. Further, the thoracic retractor provides a platform to which cardiovascular retractors and other surgical equipment can be attached and anchored.

A fairly recent type of open-heart surgical procedure to correct atrial fibrillation is the so-called Maze procedure. The January, 2000 issue of "Seminars in Thoracic and Cardiovascular Surgery" is a compendium of articles about the Maze procedure published by W.B. Saunders Publishing Company, and is hereby incorporated by reference in its entirety. In the Maze procedure as originally practiced, precise incisions were created in the right and left atria. Because scar tissue can block errant electrical impulses, the scar tissue generated by the incisions can block routes of errant electrical impulses responsible for atrial fibrillation. Specifically, the scar tissue can direct normal sinus impulses to travel to the atrioventricular node as they normally should. Recently, the Maze procedure has been altered to focus mainly on the left atrium, because the vast majority of irregular foci come from areas around the four pulmonary veins and those veins are connected to the left atrium.

During the Maze procedure as presently practiced, the incised myocardium is retracted to move portions of the heart tissue and to expose the pulmonary veins and the artial appendage. The retraction can be accomplished manually by an assistant using a hand-held retractor blade that contacts the tissue adjacent to the mitral valve. Unfortunately, manual retraction is quite undesirable for a number of reasons, including the need for the continual presence of an assistant to manipulate the retractor, and the inconsistency and variability of the retraction so provided.

An alternative technique to retract the heart tissue and expose the pulmonary veins and the atrial appendage is to use a plurality of relatively narrow, short retractor blades that are mounted onto the thoracic retractor. The retractor blades are not properly configured to retract the heart tissues to perform the Maze procedure. The previously known retractors blades cooperate with each other to retract and retain the heart tissue in a retracted position for the duration of the procedure. Each of the blades (up to three or more in number) must be individually placed and set by a surgeon to contact the inner heart wall adjacent to the mitral valve and the pulmonary veins so as to retract the heart tissue and expose the pulmonary veins and the atrial appendage. Placing and setting each of the blades takes a certain amount of time. In addition, each of the blades places a localized pressure on the heart tissue. Desirably, a retraction technique would be available that would decrease the time required to perform the surgical procedure as well as to decrease and delocalize the pressure on the heart tissue.

SUMMARY OF THE INVENTION

In response to the foregoing concerns, the present invention provides new and improved surgical retractors and a new and improved technique for performing heart surgery. The surgical retractors of the present invention are especially adapted for use in performing atrial fibrillation reduction surgery, typically the Maze procedure.

One of the surgical retractors according to the invention is especially adapted to retract the mitral valve and adjacent tissues ("mitral valve retractor") during a surgical procedure. The mitral valve retractor includes a handle that defines an axis and has first and second ends. A large, elongate retractor blade is secured to the second end of the handle. The blade projects from the handle at a predetermined angle relative to the handle axis. The blade extends toward and across the mitral valve, the lower annulus of the mitral valve, and the tissues adjacent thereto. Retracting the handle causes the retractor blade to contact and retract the exposed mitral valve and adjacent tissues. In the preferred embodiment, the blade tapers from a, narrow portion adjacent the second end of the handle to a wider portion remote from the second end of the handle.

Another surgical retractor according to the invention ("left atrial appendage retractor") is configured to retract a portion of the left atrium adjacent the atrial appendage to thereby expose, for example, the pulmonary veins and left atrial appendage. The left atrial appendage retractor includes a handle that defines an axis and has first and second ends. A narrow, elongate retractor blade is secured to the second end of the handle. The blade projects from the handle at a predetermined angle relative to the handle axis. The blade extends deep into the heart to contact and retract a portion of the heart near the atrial appendage. Retracting the handle causes the blade to contact and retract the atrium so as to expose the pulmonary veins and/or atrial appendage. Preferably, the blade has an end portion that extends back upon itself in order to better engage the heart tissues.

The present invention includes alternate forms of the referenced retractors. For example, the mitral valve retractor can be provided with an adjustable blade, and the left atrial appendage retractor can be provided with an angled handle to provide different access to the pulmonary veins.

The present invention also provides a method of performing an open-heart surgical procedure. The method includes incising a heart so as to expose a mitral valve. The mitral valve retractor is oriented relative to the mitral valve so that the mitral valve retractor extends toward and across all or part of the mitral valve. The mitral valve retractor contacts the mitral valve, tissues adjacent to the mitral valve, and/or the lower annulus of the mitral valve. The mitral valve retractor is moved while in contact with the mitral valve so that an interior portion of the heart is made accessible. Similarly, the left atrial appendage retractor is used to contact and retract the tissues in the region of the left atrial appendage. The retractors preferably will be used in conjunction with one another, although they can be used separately, if desired.

BRIEF DESCRIPTION OF THE DRAWINGS

The foregoing and other features and advantages of the invention will be apparent from the following description and claims, including the accompanying drawings, wherein:

DESCRIPTION OF THE PREFERRED EMBODIMENT

Figure 1:
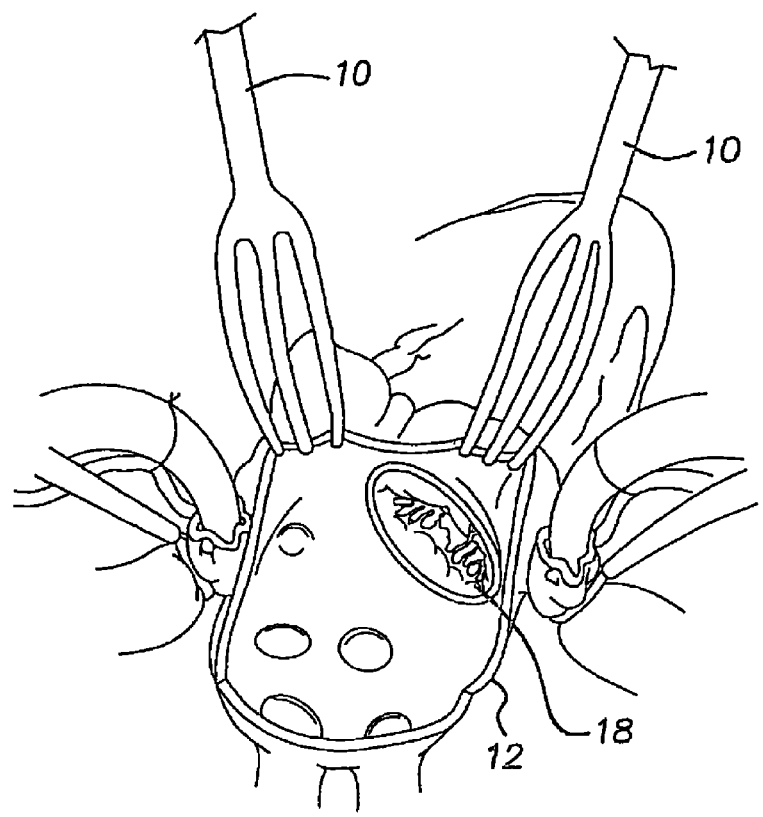
FIG. 1 is a view of prior art cardiovascular refractors being used to retract portions of a patient's heart.

FIG. 1 shows a plurality of retractors 10 of a prior art apparatus for use during a surgical procedure on a heart 12. The retractors 10 pull on various inner surfaces of the heart wall so as to retract the heart tissues and thus expose the mitral valve, which is indicated by the reference numeral 18.

Figure 2:
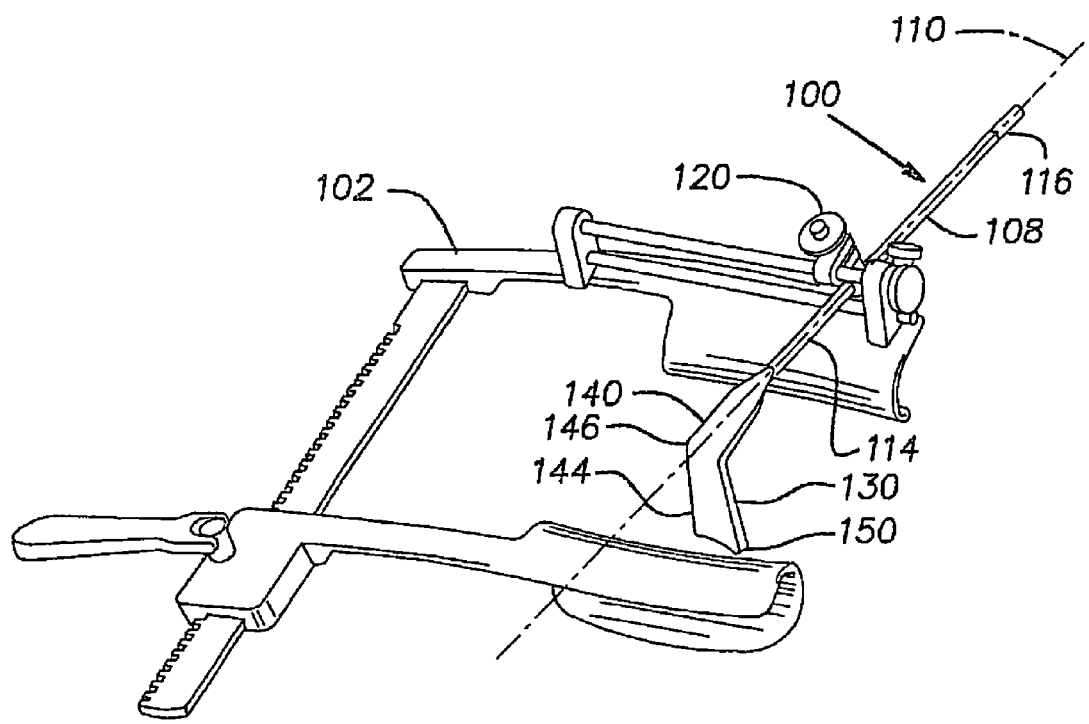
FIG. 2 is a perspective view of a known thoracic retractor to which a retractor according to the invention is attached.

A surgical retractor 100 comprising a first embodiment of the present invention is shown in FIG. 2. The retractor 100 is a mitral valve retractor adapted for use with a thoracic retractor 102. Suitable thoracic retractors are commercially available from Kapp Surgical Instrument, Inc. (Cleveland, Ohio). The retractor 100 in accordance with the present invention is operable to retract and expose, for example, a mitral heart valve (not shown) and the inside cavity of a heart during an open-heart surgical procedure. A Maze procedure is an example of such an open-heart surgical procedure. The retractor 100 differs from the prior art generally in that it is configured to contact the mitral valve and optionally the adjacent heart tissues rather than the heart wall's inner surface.

Specifically, the retractor 100 includes a 0.6 centimeter (0.25 inch) diameter surgical stainless steel rod or handle 108, which defines a handle axis 110. The handle 108 has first and second ends 114, 116. The handle second end 116 is adapted to be clamped to the thoracic retractor 102. A clamp 120 secures the handle second end 116 to the thoracic retractor 102.

A retractor blade 130 is secured or welded to the handle first end 114 and is preferably formed of stainless surgical steel. In this embodiment, the blade 130 has a proximal portion 140, and a one-piece, solid distal portion 144. The proximal portion 140 is secured to the handle first end 114, and extends away from the handle 108 to a bend 146. The distal portion 144 extends from the bend 146 to a generally flat terminal end 150. The proximal portion 140 is preferably about 5.7 cm (2.25 inches) long. The distal portion 144 is preferably in a range of about 11.4 cm (4.5 inches) to about 19 cm (7.5 inches) long, and is more preferably 13.3 cm (5.25 inches) long. Accordingly, the distal portion 144 is longer than conventional retractors used in similar type applications. Rather than pinning back portions of the heart and creating localized areas of pressure, the distal portion 144 extends deeper into the incised heart and applies pressure during retraction over a relatively larger surface area.

During operation, the blade 130 is oriented relative to the mitral heart valve that is exposed during the surgical heart procedure. Specifically, the distal portion 144 is placed adjacent to and across the exposed mitral valve and the heart tissues surrounding and adjacent to the mitral valve. The distal portion 144 is contacted against the mitral valve and optionally the adjacent heart tissues. The retractor 100 is moved along the axis 110 relative to the thoracic retractor 102 to retract the mitral valve and expose the interior of the heart.

Specifically, the clamp 120 is loosened and the handle 108 is slid through the clamp 120 relative to the thoracic retractor 102. The movement of the handle 108 contacts the distal portion 144 against the mitral valve and thereby retracts the mitral valve. When a desired level of retraction is obtained, the clamp 120 is tightened and the handle 108 is secured in place. The mitral valve and the adjacent heart tissues are retracted and held in place by the distal portion 144 until the clamp 120 is again loosened.

Figure 3:
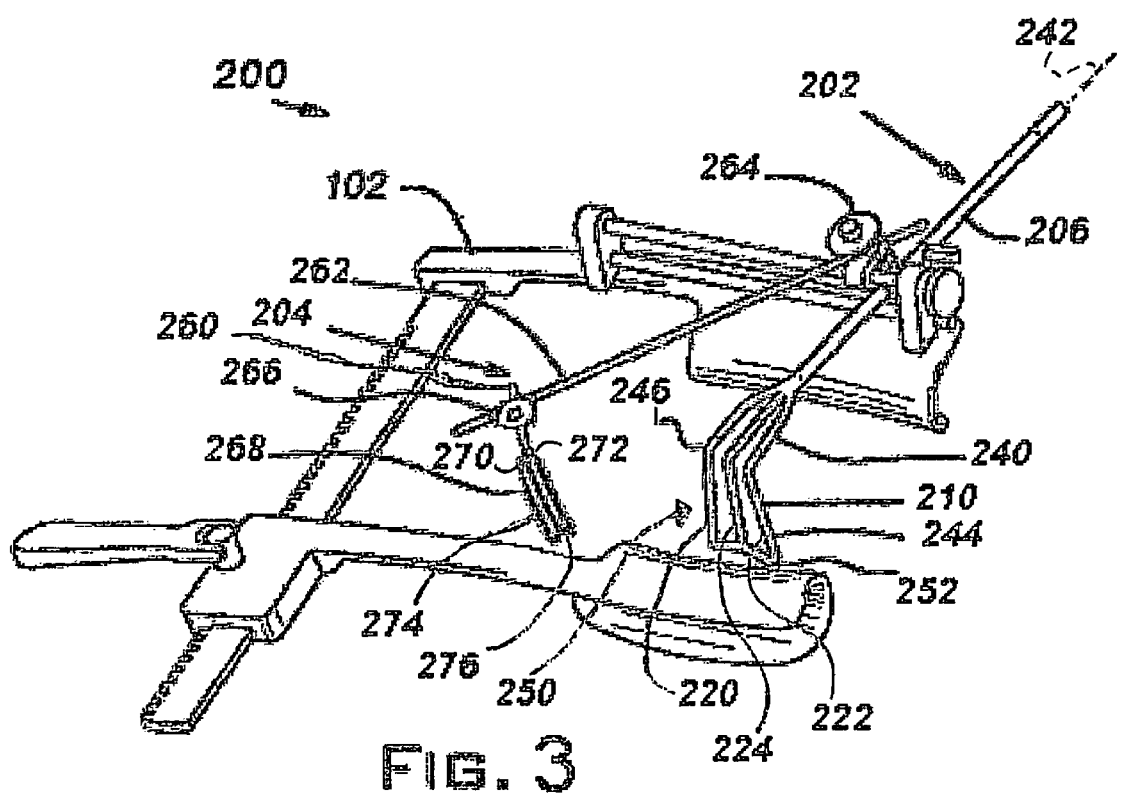
FIG. 3 is a view similar to FIG. 2 showing two retractors according to the invention.
Figure 4:
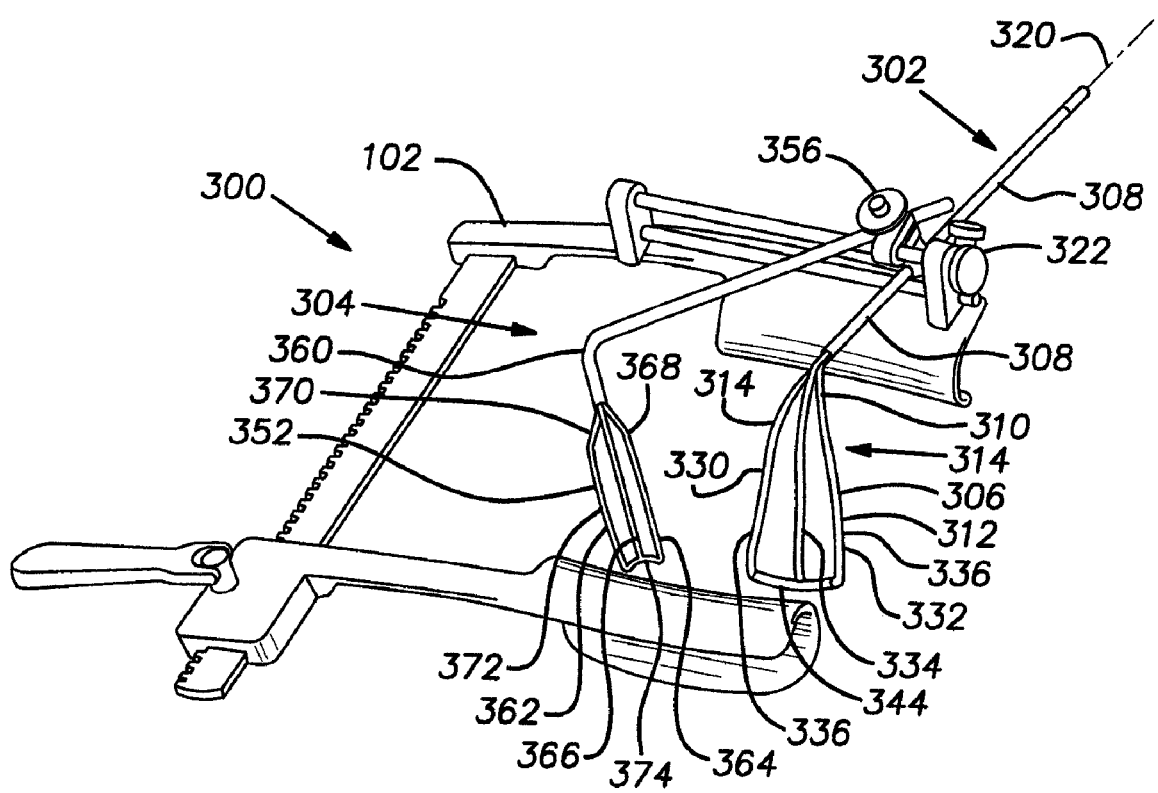
FIG. 4 is a view similar to FIG. 3 showing alternative embodiments of retractors according to the invention.
Figure 5:
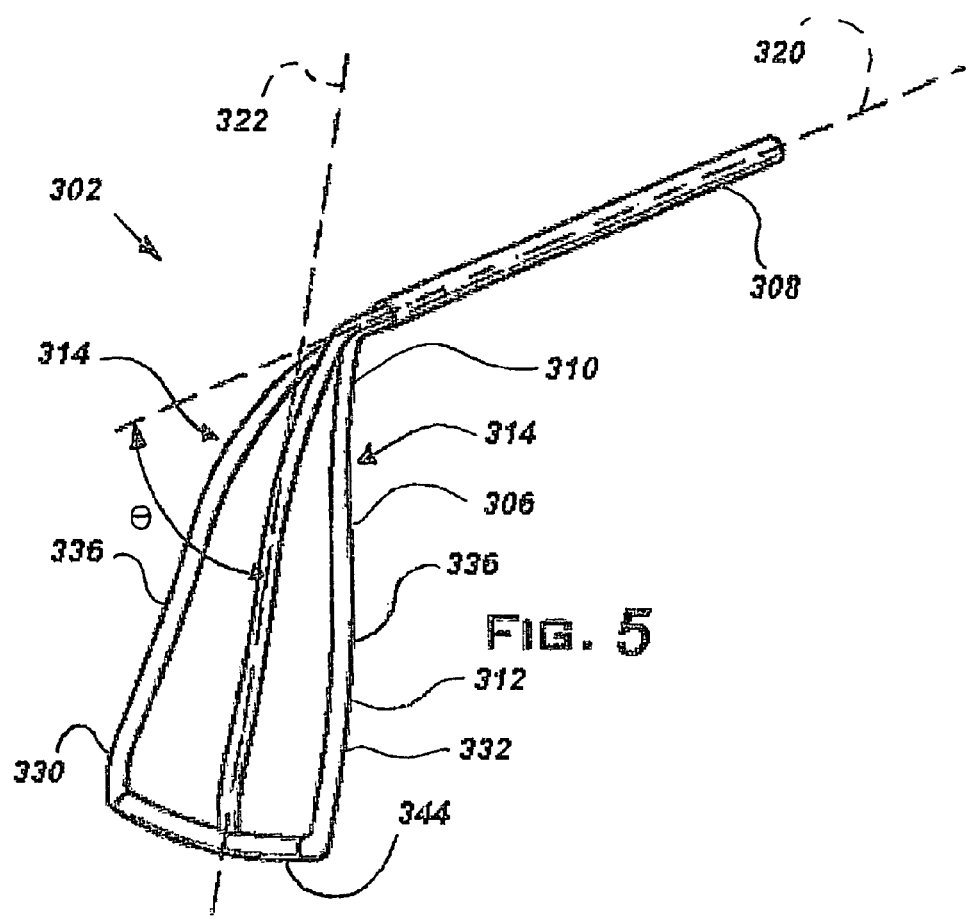
FIG. 5 is a perspective view of one of the retractors shown in FIG. 4.
Figure 6:
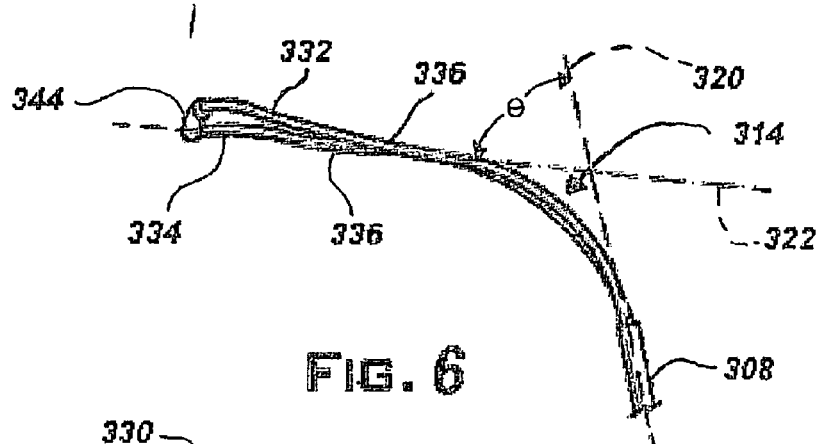
FIG. 6 is a side view of a portion of the retractor shown in FIG. 5.
Figure 7:
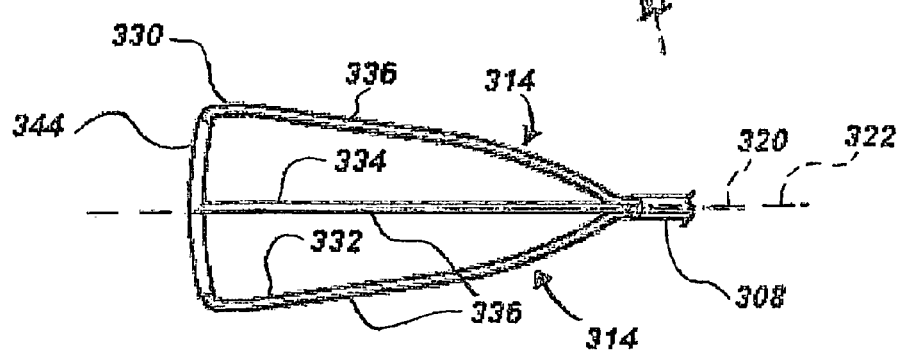
FIG. 7 is a top plan view of a portion of the retractor shown in FIG. 5.
Figure 8:
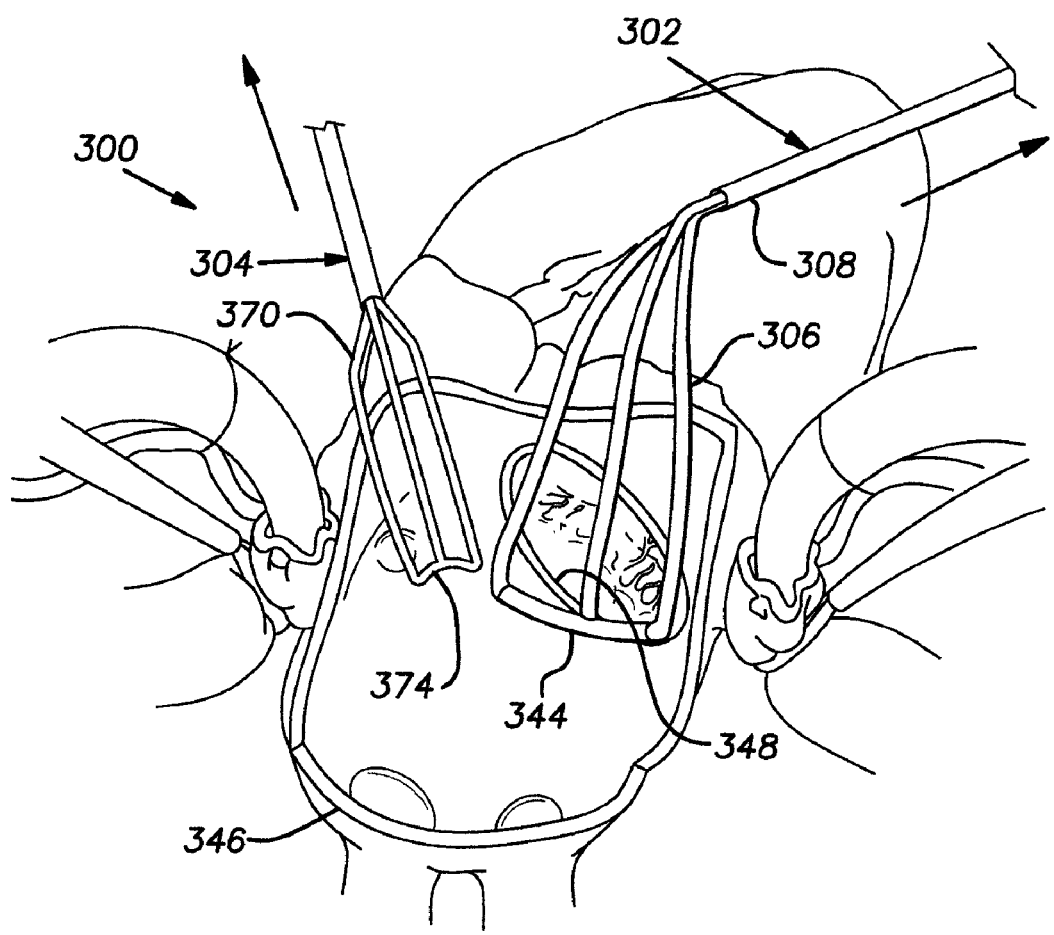
FIG. 8 is an enlarged view of the retractors shown in FIG. 4 in an operative position engaging tissues of an incised heart.

A retractor system 200 having first and second retractors 202, 204 and comprising a second embodiment of the invention is shown in FIG. 3. The first retractor 202 has a handle 206 and a blade 210. The blade 210 differs from the solid blade 130 by including a plurality of spokes (preferably a first spoke 220, a second spoke 222, and a middle, third spoke 224).

The blade 210 is formed of a malleable metal and defines a proximal portion 240 that is generally co-planar with a handle axis 242, which is defined by the handle 206. The blade 210 further defines a distal portion 244 that is angled relative to the handle axis 242. A first bend 246 defines a boundary between the proximal and distal portions 240, 244. The spokes 220, 222, 224 of the distal portion 244 are thus also angled relative to the handle axis 242. The first and second spokes 220, 222 each have a second bend 250 so that the first and second spokes 220, 222 are about equal distances away from the center spoke 224 in generally opposite directions relative to each other.

The blade 210 also includes a tip 252 that is curved along its length to define an arc. The tip 252 is preferably welded to each of the ends of the spokes 220, 222, 224. The tip 252 is preferably longer than the diameter of the mitral valve, that is, in a range of about 3.2 cm (1.25 inches) to about 5 cm (2 inches). More preferably, the tip 252 has a length of about 4.5 cm (2.75 inches). Thus, the area of the distal portion 244 is larger than, or about the same size as, an area defined by the mitral valve and the heart tissues surrounding and adjacent to the mitral valve. The tip 252 preferably has a surface profile or texture that is knurled, ridged or serrated. The texture of the tip 252, if present, can facilitate grabbing tissue and maintaining a grip once established.

The spokes 220, 222, 224 form angles in the range of about 20 to about 65 degrees relative to the handle axis 242. In this embodiment, the angles are about 60 degrees relative to the handle axis 242. The spokes 220, 222, 224 are not coplanar with each other. The middle, third spoke 224 is slightly longer than the first and second spokes 220, 222, and the third spoke 224 is angled slightly more than the first and second spokes 220, 222. Accordingly, the tip 252 defines a compound curve or arc that contacts an end of each of the spokes 220, 222, 224.

The spokes 220, 222, 224 each define a third bend 250 disposed between the first bend 246 and the tip 252. The third bend 250 forms the distal portion 244 as a convex shape so that when contacted against the concave inner surface of the heart, the distal portion 244 closely matches the shape of the heart. Contact stress is distributed over the contacted area of the heart inner surface.

In a preferred embodiment, the combined length of the distal and proximal portions 240, 244 is preferably about 11.5 cm (4.75 inches). Further, the length of the distal portion 244 is about 7.5 cm (3 inches), and the length from either second bend 250 to the tip 252 is about 2.5 cm (1 inches).

The second retractor 204 is also mounted to the thoracic retractor 102. The second retractor 204 includes first and second handles 260, 262, first and second clamps 264, 266, and a blade 268 secured to the first handle 260.

A first clamp 264 holds the second handle 262 to the first handle 260. The retractor blade 268 is attached to the opposite end of the first handle 260. The handles 260, 262 are preferably stainless surgical steel and have lengths in a range of about 2.5 cm (1 inch) to about 25 cm (10 inches) and a diameter of about 0.6 cm (0.25 inches).

The second retractor blade 268 is narrow relative to the first retractor blade 210, but is about as deep and is otherwise similar in configuration. That is, the blade 268 has curve 270 that defines proximal and distal portions 272, 274 with relation to the handle 262. Preferably, the combined length of the proximal and distal portions 272, 274 is about 9.5 cm (3.75 inches) to about 19 cm (7.6 inches), and the length of the distal portion 274 is about 7.5 cm (3.0 inches).

A second tip 276 is attached to the ends of three spokes that form the body of the second blade 268. The second tip 276 has a curve that forms an arc opening away from the first handle 260. Accordingly, the second blade 268 has a convex surface configured to contact the concave inner surface of the left atrium. The second tip 276 can have a textured surface profile the same as the first tip 252.

During open-heart surgical procedures performed in accordance with the present invention, the distal portion 244 of the first retractor 202 is oriented relative to an incised heart so as to extend toward and across a mitral valve and tissue surrounding the mitral valve. The distal portion 244 is contacted against the mitral valve and the tissues surrounding the mitral valve so as to move and retract the mitral valve and the tissues surrounding the mitral valve. The retraction exposes the interior of the heart and maintains the exposure for a desired period of time. The curvature of the tip 252 distributes stress evenly across heart tissue during the contacting and retraction so as to alleviate and decrease the amount of stress relative to tips that do not have such an arced configuration.

A retractor system 300 comprising a third embodiment of the invention is shown in FIGS. 4-8. The retractor system 300 includes first and second retractors 302, 304.

The first retractor 302 includes a blade 306 mounted to a handle 308. The blade 306 has proximal and distal portions 310, 312 that are defined by a bend 314. The proximal and distal portions 310, 312 together measure about 19 cm (7.5 inches) long. The proximal portion 310 is centered on a handle axis 320, which is defined the handle 308. A clamp 322 releaseably secures the handle 308 to the thoracic retractor 102.

The distal portion 312 includes first, second and third spokes 330, 332, 334 that preferably have a length in a range of about 12 cm (4.75 inches) to about 13.3 cm (5.25 inches) long and are about 0.3 cm (0.1 inch) wide. The spokes 330, 332, 334 extend in generally straight lines from the first bend 314 at the intersection of the proximal and distal portions 310, 312 to a tip 344 at the opposite end of the distal portion 312.

A distal portion axis 322 is defined by the third spoke 334, and forms an angle θ in the range of from about 35 to about 95 degrees relative to the handle axis 320, and preferably forms an angle of about 50 degrees. Parts of the distal portion 312, for example, the first and second spokes 330, 332, are not coplanar with the distal portion axis 322, but are generally aligned with the distal portion axis 322. The middle, third spoke 334, which is coplanar with the distal portion axis 322, is at a slightly larger angle with reference to the handle axis 320 than the first and second spokes 330, 332.

The spokes 330, 332, 334 form a third bend 336 in a region located between the first bend 314 and the tip 344. The third bend 336 preferably flares the distal portion 312 into an "S"-like configuration, so that the spokes 330, 332, 334 form a smaller angle adjacent to the tip 344 relative to the angle ⊖ formed by the first bend 314.

The tip 344 is generally smooth and preferably about 3.2 cm (1.25 inches) long, and about 0.5 cm (0.2 inches) wide, and is oriented generally perpendicular to the spokes 330, 332, 334. The surface of the tip 344 can alternatively have a texture or profile like the tip 252 of the previous embodiment. Solder is preferably used to secure the tip 344 to the spokes 330, 332, 334. Because the spokes 330, 332, 334 are not co-planar, and because the middle spoke 334 is slightly longer than the outer spokes 330, 332, the tip 344 forms a compound curve. The curve of the tip 344 follows the concave interior surface of the left atrium of an incised heart 346 to increase the contact are of the blade 306 with the interior surface of the heart 346. Preferably, the tip 344 is sized and shaped to approximate the interior surface of the left atrium in the region of the lower annulus 348 of the mitral valve.

The second retractor 304 also includes a handle 350 and a blade 352. The handle 350 mounts at a first end to the thoracic retractor 102 via a clamp 356, and the blade 352 is secured, preferably by welding, to the opposite end of the handle 350. Disposed between the ends of the handle 350 is a bend 360 having an angle in the range of about 25 to 95 degrees, and preferably about 45 degrees. The handle 350 is otherwise generally like the handle 308.

The second blade 352 has a plurality of spokes, preferably three spokes (first, second outer spokes 362, 364 and a third, middle spoke 366). The spokes 362, 364, 366 have a bend 368 that defines a proximal portion 370 of the second blade 352 attached to the second handle 350, and distal portion 372 that defines a tip 374. The distal portion 372 has a length preferably in a range of from about 5 cm (2 inches) to about 8 cm (3.25 inches) to extend deeply into the incised heart and contact the inner surface of the left atrium spaced from the first blade 306.

The tip 374 of the second blade 352 defines an arc, about 2.5 cm (1 inch) across, opening away from the handle 350. Accordingly, the convex side of the tip 374 is configured to match the concave inner surface of the left atrium and to grip the heart tissue proximate to the pulmonary veins.

During open-heart surgical procedures performed in accordance with the present invention, the heart is incised to open the left atrium. The distal portion 312 is oriented relative to an incised heart so as to extend toward and across a mitral valve and tissues surrounding the mitral valve. The distal portion 312 is contacted against the mitral valve, the lower annulus of the mitral valve, and tissue surrounding the mitral valve so as to move and retract the mitral valve and the tissues surrounding the mitral valve. The retraction exposes the interior of the heart and maintains the exposure for a desired period of time. The tip arc can distribute stress to the heart tissues during the contacting and retraction so as to alleviate and decrease the amount of stress relative to a tip that does not have such an arc configuration.

At about the same time as the first retractor 302 is employed, the second retractor 304 is oriented relative to the heart and the thoracic retractor 102 so that the second blade 352 contacts the inner surface of the left atrium proximate to the pulmonary veins. The second blade 352 retracts the heart wall and exposes the pulmonary arteries. The clamp 356 is tightened to secure the second retractor 304 in place. The second retractor 304 is thus contacted against the heart tissue to expose a patient's left pulmonary veins and atrial appendage during, for example, a Maze procedure.

Thus, the first and second retractors 302, 304 cooperate to maintain access to the interior of the left atrium during the surgical procedure. After the procedure, the clamps 322, 356 are loosened and the retractors 302, 304 are removed from the heart.

Figure 9:
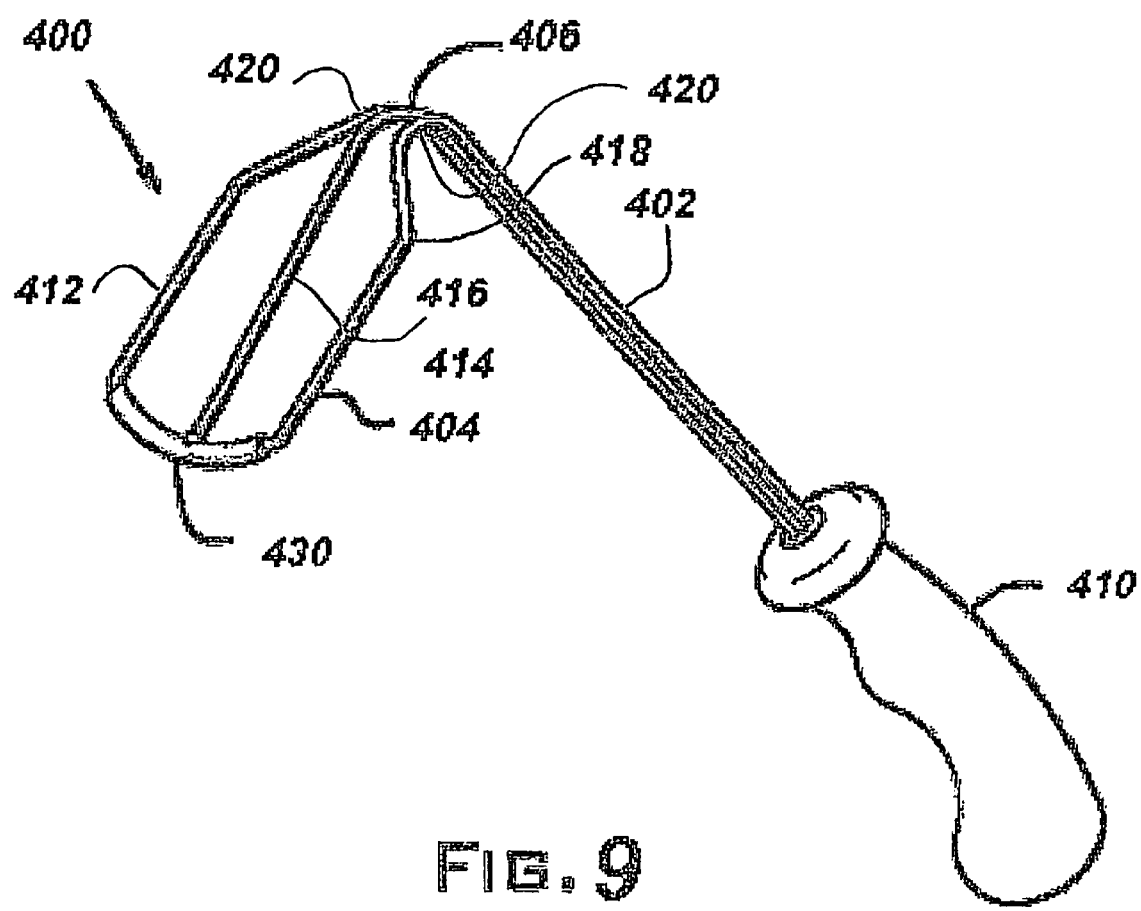
FIG. 9 is a perspective view of a retractor according to the invention suitable for manual use.

A hand retractor 400 comprising a manually operable embodiment of the present invention is shown in FIG. 9. The hand retractor 400 includes a handle 402 and a blade 404. The handle 402 and the blade 404 are separated by a bend portion 406 at an end of the handle 402. The bend portion 406 angles the blade 404 relative to the handle 402. A grip 410 is attached to the opposite end of the handle 402 from the bend portion 406.

The blade 404 preferably has three wire spokes (two outer spokes 412, 414, and a third, middle spoke 416). The outer spokes 412, 414 each have a second bend 418 and a third bend 420 so that the body of the outer spokes 412, 414 is generally parallel with the middle spoke 416. The blade 404 has a distal tip 430, which is generally like the tip 344 described hereinabove.

The hand retractor 400 does not secure to a thoracic retractor, but is manipulated by hand, preferably by a surgical assistant, during a surgical procedure. Otherwise, the hand retractor 400 performs in substantially the same manner as the first retractor 302 described hereinabove.

Figure 10:
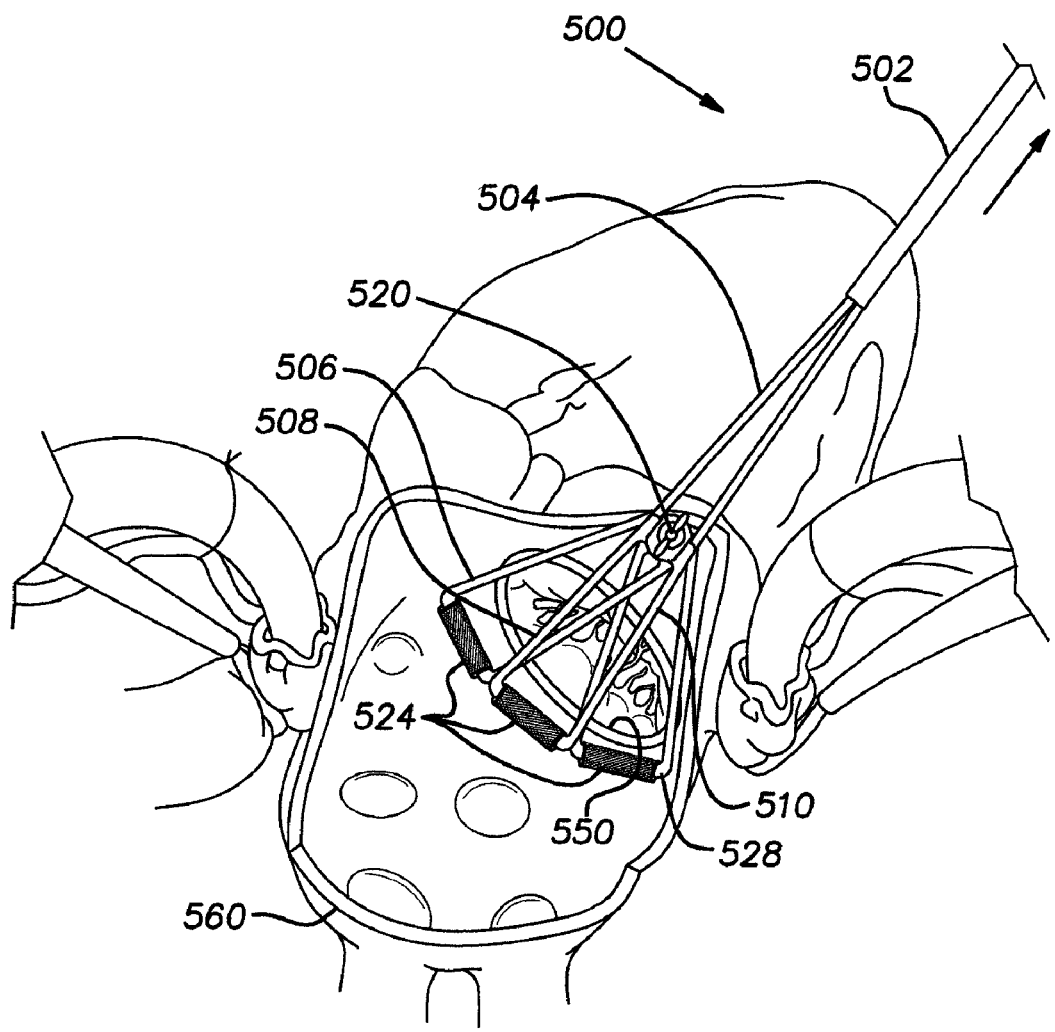
FIG. 10 is an perspective view of another retractor according to the invention in an operative position engaging tissues of an incised heart.
Figure 11:
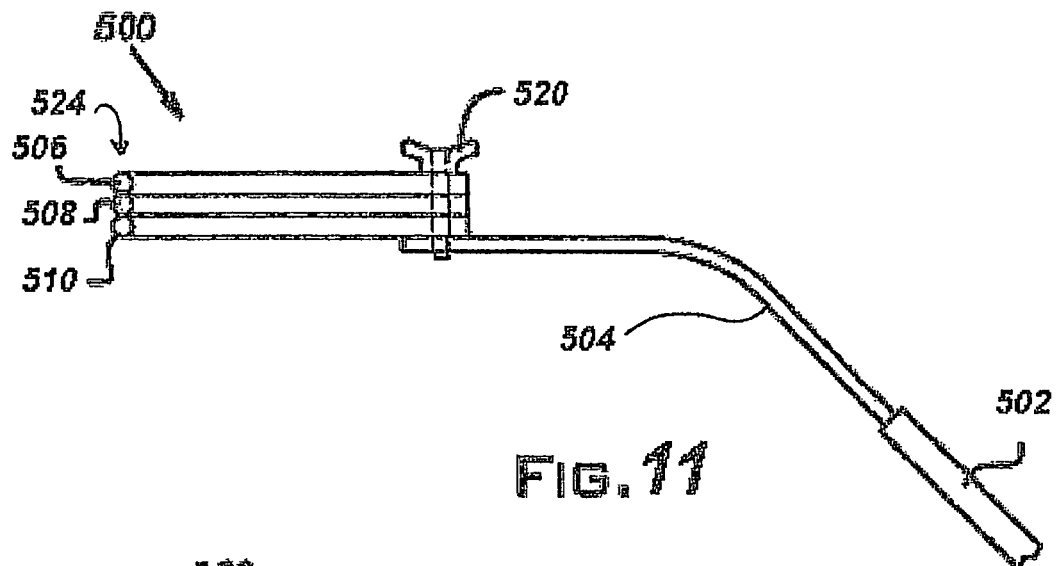
FIG. 11 is a side view of the retractor shown in FIG. 10.
Figure 12:
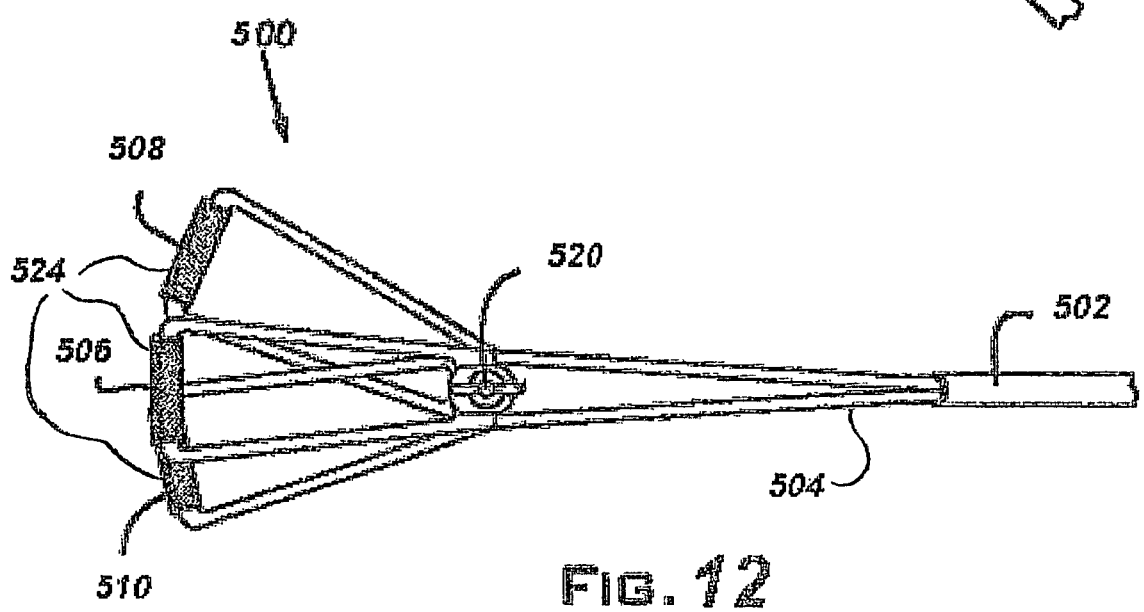
FIG. 12 is a top plan view of the apparatus shown in FIG. 10.

A surgical retractor 500 comprising a preferred embodiment of the present invention is shown in FIGS. 10-12. In this embodiment, the retractor 500 includes a handle 502, an extension 504, and a plurality of arrangeable blade portions, preferably three blade portions 506, 508, 510. The blade portions 506, 508, 510 are each preferably about 5.6 cm (2.2 inches) long and about 2 cm (0.8 inches) wide.

A screw clamp 520 includes a pivot and can loosen and tighten, and thereby allow pivotal movement when loosened, and clamp the blade portions 506, 508, 510 into a desired position relative to each other when tightened.

A tip 524 secures to an end of each of the blade portions 506, 508, 510. Each tip 524 is generally handle-shaped and generally straight along its 1.5 cm (0.6 inch) length. The blade portions 506, 508, 510 can fan out at their distal ends 528 to increase the total surface area of the blades 506, 508, 510 to be larger than an area of the interior of the atrium that includes a mitral valve 550.

During use, the retractor 500 is affixed to a thoracic retractor (not shown). The handle 502 is extended from the thoracic retractor to the incised heart 560. The blade portions 506, 508, 510 are spread out in a generally fan-like configuration by loosening the clamp 520 and rotating the blade portions 506, 508, 510 around the pivot. When the desired configuration is achieved, the clamp 520 is screwed down to tighten onto the blade portions 506, 508, 510 and thus immobilize the blade portions 506, 508, 510 relative to each other in the generally fan-like configuration.

The blade portions 506, 508, 510 are positioned generally over the mitral valve 550 and surrounding heart tissue in the incised heart 560. The mitral valve 550 and surrounding heart tissue is then retracted by contacting the blade portions 506, 508, 510 against the mitral valve 550 and surrounding heart tissue and moving the blade portions 506, 508, 510 in the direction indicated by the directional arrow. The handle 502 is secured to the thoracic retractor to maintain the retractor 500 in a desired position and orientation. Accordingly, the retracted section of the heart exposes the interior surface of the left atrium, and the retractor 500 thus maintains the exposure as long as is desirable.

In alternative embodiments, a retractor similar to the retractor 500 has curved blade portions. The curved blade portions nest against each other when folded and aligned with each other. The curved blade portions pivot at their base to fan out at the blade tips. Similar to the retractors described above, the blade portions extend toward and across the mitral valve in the incised heart and the surrounding heart tissue. Retracting the blades subsequently retracts the portion of the heart containing the mitral valve. The blade portions are oriented such that the curve of the blades follows the concave interior of an incised heart.

The embodiments described herein are examples of structures, systems and methods having elements corresponding to the elements of the invention recited in the claims. This written description may enable those skilled in the art to make and use embodiments having alternative elements that likewise correspond to the elements of the invention recited in the claims. The intended scope of the invention thus includes other structures, systems and methods that do not differ from the literal language of the claims, and further includes other structures, systems and methods with insubstantial differences from the literal language of the claims.

What is claimed is:

1. A surgical retractor for use in a surgical procedure on an incised heart having a mitral valve and pulmonary veins that communicate with the left atrium, comprising:
   a handle defining an axis and having first and second ends; and
   a large, elongate blade having a proximal portion and a distal portion, the proximal portion being secured to the second end of the handle and being co-planar with the axis of the handle, the distal portion being configured to extend toward and across the mitral valve and to contact the mitral valve, tissue adjacent to the mitral valve, and the lower annulus of the mitral valve, the distal portion having a length within the range of from about 7.5 cm to about 19 cm and a width within the range of from about 3.2 cm to about 5 cm, the distal portion projecting from the proximal portion at an angle in the range of about 20 to about 95 degrees measured in an anticlockwise direction relative to the axis of the handle, whereby the distal portion is generally L-shaped relative to the axis of the handle, the distal portion generally lying in a single plane and defining a tip portion, the tip portion having a configuration of the left atrium in the region of the lower annulus of the mitral valve, whereby the configuration allows for decreased and delocalized pressure on the mitral valve and adjacent tissue, the tip portion having opposed ends and a center portion, the ends being out of the plane in which the distal portion lies and being disposed closer to the handle than the center portion, whereby retracting the handle causes the blade to contact and retract the mitral valve and the adjacent tissue.

2. The surgical retractor as defined in claim 1, wherein the blade comprises a plurality of spokes.

3. The retractor as defined in claim 2, wherein the spokes are disposed generally parallel with each other.

4. The retractor as defined in claim 2, wherein the spokes diverge from a narrower width at the proximal portion to a wider width at the distal portion.

5. The surgical retractor as defined in claim 1, wherein the tip portion has a surface finish that is selected from the group consisting of smooth, serrated, and knurled.

6. The surgical retractor as defined in claim 1, wherein the distal portion generally lies in a plane that is oriented relative to the axis of the handle at an angle within the range of from about 20 to about 65 degrees.

7. The surgical retractor as defined in claim 1, wherein the blade is formed of a malleable metal such that it can be positioned relative to the axis of the handle in any desired position.

8. The surgical retractor as defined in claim 1, further comprising a grip attached to the first end of the handle, whereby the retractor can be manipulated manually.

9. The surgical retractor as defined in claim 1, wherein the blade has a width and includes:
   a plurality of fan blade portions movable relative to each other, each fan blade portion having a proximal end and a distal end; and
   a pivoted connection between the proximal ends of the fan blade portions and the second end of the handle, the pivoted connection permitting the width of the blade to be adjusted.

10. The surgical retractor as defined in claim 9, wherein the proximal end of each fan blade portion includes an opening, and further comprising a fastener that extends through the openings when the openings are aligned, the fastener, upon being tightened, applying a compressive force to the fan blade portions so as to retain them in any desired position.

11. The surgical retractor as defined in claim 1, wherein the blade, when viewed from the side, generally defines a convex curve relative to the axis of the handle in the region of the proximal portion and generally defines a concave curve relative to the axis of the handle in the region of the distal portion.

12. A surgical retractor for use in a surgical procedure on an incised heart having a mitral valve, pulmonary veins that communicate with the left atrium, and an atrial appendage, comprising:
   a handle defining an axis and having first and second ends; and
   a narrow, elongate blade having a proximal portion and a distal portion, the proximal portion being secured to the second end of the handle and being co-planar with the axis of the handle, the distal portion being configured to extend deeply into the incised heart and to contact a portion of the atrium near the atrial appendage, the distal portion having a length within the range of from about 5 cm to about 8 cm and a width of about 2.5 cm, the distal portion projecting from the proximal portion at an angle in the range of about 20 to about 95 degrees measured in an anticlockwise direction relative to the axis of the handle, whereby the distal portion is generally L shaped relative to the axis of the handle, the distal portion generally lying in a single plane and defining a tip portion, the tip portion having a configuration that approximates that of the left atrium in the region of the atrial appendage, whereby the configuration allows for decreased and delocalized pressure on the mitral valve and adjacent tissue and whereby retracting the handle causes the blade to contact and retract the atrium so as to expose the pulmonary veins.

13. The surgical retractor as defined in claim 12, wherein the blade comprises a plurality of spokes.

14. The surgical retractor as defined in claim 13, wherein the spokes are disposed generally parallel with each other.

15. The surgical retractor as defined in claim 13, wherein the spokes diverge from a narrower width at the proximal portion to a wider width at the distal portion.

16. The surgical retractor as defined in claim 12, wherein the tip portion has a surface finish that is selected from the group consisting of smooth, serrated, and knurled.

17. The surgical retractor as defined in claim 12, wherein the tip portion is concave relative to the handle axis.

18. The surgical retractor as defined in claim 12, wherein the distal portion generally lies in a plane that is oriented relative to the axis of the handle at an angle within the range of from about 20 to about 65 degrees.

19. The surgical retractor as defined in claim 12, wherein the blade is formed of a malleable metal such that it can be adjusted relative to the axis of the handle in any desired position.

20. The surgical retractor as defined in claim 18, wherein the handle comprises first and second segments, the first segment being disposed remote from the blade and the second segment being connected to the blade, the first and second segments defining, respectively, first and second longitudinal axes, the first and second axes generally lying in a common plane and being positioned relative to each other at an angle of about 45 degrees.

21. A surgical retractor system for use in a surgical procedure on an incised heart having a mitral valve, pulmonary veins communicating with the left atrium, and an atrial appendage, comprising:

first and second retractors, the retractors each having a handle and a blade, the handle of each retractor defining an axis and having first and second ends, and the blade of each retractor having a proximal portion and a distal portion, the proximal portion being secured to the second end of the handle and projecting at a predetermined angle relative to the axis of the handle;

the distal portion of the first retractor blade generally lying in a single plane and having a configuration that forms an angle in the range of from about 20 to 95 degrees measured in an anticlockwise direction relative to the axis of the handle, whereby the configuration generally has an L-shape relative to the axis of the handle that closely matches the concave inner surface of the heart, the distal portion being configured to extend toward and across the mitral valve to contact the mitral valve and to retract the mitral valve and adjacent tissues; and the distal portion of the second retractor blade having a shape that closely matches the concave inner surface of the heart, the distal portion being configured to extend deep into the incised heart to contact a portion of the atrium near the atrial appendage and to retract the atrium so as to expose the pulmonary veins.

22. A method of performing an open-heart surgical procedure, comprising the steps of:

incising a heart so as to expose the mitral valve;

providing a first retractor having a handle that defines an axis, relatively large, elongate blade with a distal portion generally lying in a single plane and having a configuration that forms an angle in the range of from about 20 to 95 degrees measured in an anticlockwise direction relative to the first retractor handle axis, whereby the configuration generally has an L-shape relative to the axis of the handle that closely matches the concave inner surface of the heart and that is configured to extend toward and across the mitral valve;

orienting the first retractor so that the distal portion of the first retractor extends toward and across the mitral valve;

moving the first retractor relative to the heart to contact the mitral valve and adjacent tissues with the distal portion and retract at least a portion of the mitral valve and adjacent tissues;

providing a second retractor having a handle that defines an axis and a relatively narrow, elongate blade with a distal portion having a shape that closely matches the concave inner surface of the heart and that is configured to extend deeply into the heart;

orienting the second retractor so that the distal portion of the second retractor is disposed in the region of the atrial appendage; and moving the second retractor relative to the heart to retract the region of the atrial appendage with the distal portion and to expose the pulmonary veins.

* * * * *